United States Patent [19]

Hayashi et al.

[11] Patent Number: 4,479,944
[45] Date of Patent: Oct. 30, 1984

[54] COMPOSITION CONTAINING PGI$_2$ ANALOGS STABILIZED

[75] Inventors: Masaki Hayashi; Katsuhiko Shuto, both of Takatsuki; Yoshitsugu Iijima, Hikone, all of Japan

[73] Assignee: Ono Pharmaceutical Co., Ltd., Osaka, Japan

[21] Appl. No.: 902,118

[22] Filed: May 2, 1978

[30] Foreign Application Priority Data

May 6, 1977 [JP] Japan .................................. 52-51278

[51] Int. Cl.$^3$ ................. C07D 307/395; A61K 31/72
[52] U.S. Cl. ..................................... 424/180; 424/285; 536/103; 549/465
[58] Field of Search ............... 260/346.22; 536/103; 549/465; 424/180, 285

[56] References Cited

U.S. PATENT DOCUMENTS 4,070,537  1/1978  Hayashi et al. ............... 260/346.22
4,232,009 11/1980  Hayashi et al. ..................... 549/465

OTHER PUBLICATIONS

Johnson et al., J.A.C.S., 99:12, Jun. 8, 1977, pp. 4182–4184.
Corey et al., J.A.C.S., 99:6, Mar. 16, 1977, pp. 2006–2008.

*Primary Examiner*—Henry R. Jiles
*Assistant Examiner*—Bernard Dentz
*Attorney, Agent, or Firm*—Stevens, Davis, Miller & Mosher

[57] ABSTRACT

Compositions which contain a PGI$_2$ analogue in solution in a solvent consisting of at least one pharmacologically-acceptable alcohol, polar aprotic solvent or middle chain triglyceride, or which are cyclodextrin clathrates of a PGI$_2$ analogue stabilise the PGI$_2$ analogues against decomposition. They are useful in the treatment of arteriosclerosis, cardiac failure or thrombosis.

20 Claims, No Drawings

COMPOSITION CONTAINING PGI₂ ANALOGS STABILIZED

This invention relates to stabilized compositions containing prostaglandin I$_2$ (PGI$_2$) analogues.

PGI$_2$ is a physiologically active substance having the following formula:

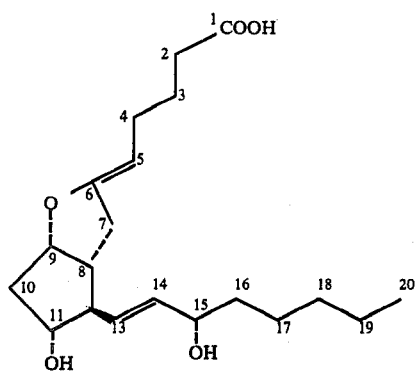

and its chemical name is (5Z,13E)-(9α,11α,15S)-6,9-epoxy-11,15-dihydroxyprosta-5,13-dienoic acid [Nature, 263, 663 (1976), Prostaglandins, 12, 685 (1976), ibid, 12, 915 (1976), ibid, 13, 3 (1977), ibid, 13, 375 (1977) and Chemical and Engineering News, Dec. 20, 17 (1976)].

It is well known that PGI$_2$ can be prepared by incubation of prostaglandin G$_2$ (PGG$_2$) or prostaglandin H$_2$ (PGH$_2$) with microsomal fraction prepared from thoracic aorta of swine, mesenteric artery of swine, rabbit aorta or the stomach fundus of rats. PGI$_2$ has a relaxing activity on the artery, which is peculiar to the artery and which does not operate on other smooth muscle. Furthermore, PGI$_2$ strongly inhibits blood platelet aggregation and has hypotensive activity.

Taking into consideration that thromboxane A$_2$ prepared by incubation of PGG$_2$ or PGH$_2$ with blood platelet microsome, has a contracting activity on the artery and an aggregating activity on blood platelets, the properties of PGI$_2$ heretofore mentioned show that PGI$_2$ fulfils a very important physiological part in a living body. Therefore, PGI$_2$ may be useful in the treatment of arteriosclerosis, cardiac failure or thrombosis.

PGI$_2$ is biosynthesized from PGG$_2$ or PGH$_2$ using the specific tissue microsomes mentioned above, and its chemical structure has been identified.

In view of its properties mentioned above, PGI$_2$ is expected to be applied for medicinal use. However, it is considered that there are the following three disadvantages to its application as a pharmaceutical:

(i) PGI$_2$ has various physiological properties as heretofore mentioned. Therefore, if one property is to be used for a pharmacological purpose, the other properties cause side-effects.

(ii) In the living body, PGI$_2$ easily loses its activities by being metabolized by PG-lytic enzymes, and its effects are transitory.

(iii) As PGI$_2$ is extremely unstable especially in thermostability, it is difficult to prepare stable pharmaceutical formulations.

Because of the aforementioned defects of PGI$_2$, widespread investigations have been carried out in order to synthesize new analogues of PGI$_2$ having a different and narrower spectrum of activities and substantially longer duration of biological activities than PGI$_2$ and we have succeeded in synthesizing better compounds than PGI$_2$ in respect of points (i) and (ii).

However, the PGI$_2$ analogues obtained, like PGI$_2$, are also unstable to heat. The cause of the instability lies in the facts that they have double bond(s) or hydroxy group(s) in their structure and that the 5, 6 and 9 positions are in an extremely unstable enol ether form. For this reason, they are significantly more unstable than other pharmaceuticals.

Further extensive research and experimentation have been carried out in order to overcome this disadvantage and to obtain stabilized preparations of PGI$_2$ analogues. As a consequence of the present investigations, it has been found that the stability is considerably improved if PGI$_2$ analogues are dissolved in a (preferably anhydrous) pharmacologically-acceptable alcohol, polar aprotic solvent or middle chain triglyceride, or are converted into clathrate compounds with α- β- or γ-cyclodextrin. The compositions of the present invention stabilise the PGI$_2$ analogues against conversion by hydrolysis into 6-keto-PGF$_{1\alpha}$ compounds.

The present invention accordingly provides a stabilized composition which contains a PGI$_2$ analogue as hereinafter defined in solution in a solvent consisting of at least one pharmacologically-acceptable alcohol, polar aprotic solvent or middle chain triglyceride, or which is a cyclodextrin clathrate of a PGI$_2$ analogue.

By the term "PGI$_2$ analogue" as used in this specification and the accompanying claims is meant, for example, compounds in which the carboxy group of PGI$_2$ is esterified or replaced by an alcohol group (—CH$_2$OH), compounds which possess carbon skeletons similar to that of PGI$_2$ with a corresponding carboxy group but in which the side chains attached to the 6- and 12-positions may be longer or shorter than those of PGI$_2$, and in which the side chain attached to the 6-position may carry an alkyl substituent and the side chain attached to the 12-position may carry an alkyl, hydroxy, chloro, cycloalkyl, phenyl or phenoxy substituent, and such compounds in which the carboxy group is esterified or replaced by an alcohol group, and corresponding 5(E)-PGI$_2$ compounds, corresponding 11-deoxy-PGI$_2$ compounds, corresponding 13,14-dihydro-PGI$_2$ compounds and corresponding trans-Δ$^2$-PGI$_2$ compounds.

By the term "pharmacologically-acceptable" as applied herein to the alcohol solvents, polar aprotic solvents and middle chain triglyceride solvents, is meant such solvents which are relatively innocuous to the animal organism and which when used in compositions according to the invention do not cause side-effects such that the beneficial properties of the PGI$_2$ or PGI$_2$ analogue are vitiated by side effects ascribable to the solvent.

Preferred compositions of the invention are those containing esters or alcohol derivatives of PGI$_2$, 2a-homo-PGI$_2$, 7a-homo-PGI$_2$, 2-nor-PGI$_2$, 2-methyl-PGI$_2$, 3-methyl-PGI$_2$, 5-methyl-PGI$_2$, 7-methyl-PGI$_2$, 15-methyl-PGI$_2$, 16-methyl-PGI$_2$, 17-methyl-PGI$_2$, 16,16-dimethyl-PGI$_2$, 17,20-dimethyl-PGI$_2$, 17-ethyl-PGI$_2$, 20-hydroxy-PGI$_2$, 16-chloro-PGI$_2$, 20-chloro-PGI$_2$, 16-methyl-20-chloro-PGI$_2$, 15-cyclopentyl-16,17,18,19,20-pentanor-PGI$_2$, 15-cyclohexyl-16,17,18,19,20-pentanor-PGI$_2$, 15-(1-butyl)cyclobutyl-16,17,18,19,20-pentanor-PGI$_2$, 15-(2-ethyl)cyclopentyl-16,17,18,19,20-pentanor-PGI$_2$, 15-(3-ethyl)cyclopentyl-16,17,18,19,20-pentanor-PGI$_2$, 15-(3-propyl)cyclopentyl-16,17,18,19,20-pentanor-PGI$_2$, 15-(3-ethyl)cyclohexyl-16,17,18,19,20-pentanor-PGI$_2$, 15-(4-ethyl)cyclohexyl-16,17,18,19,20-pentanor-PGI$_2$, 16-cyclohexyl-17,18,19,20-tetranor-PGI$_2$, 16-cyclopentyl-18,19,20-trinor-PGI$_2$, 17-cyclohexyl-18,19,20-trinor-PGI$_2$, 17-cyclohexyl-19,20-dinor-PGI$_2$, 16-methyl-17-cyclohexyl-18,19,20-trinor-PGI$_2$, 19-cyclohexyl-20-nor-PGI$_2$, 16-phenyl-17,18,19,20-tetranor-PGI$_2$, 16-phenoxy-17,18,19,20-tetranor-PGI$_2$, 16-(4-chlorophenoxy)-17,18,19,20-tetranor-PGI$_2$, 16-(3-trifluoromethylphenoxy)-17,18,19,20-tetranor-PGI$_2$ and the corresponding (5E)-PGI$_2$ analogues, corresponding 11-deoxy-PGI$_2$ analogues, corresponding 13,14-dihydro-PGI$_2$ analogues and corresponding trans-$\Delta^2$-PGI$_2$ analogues and cyclodextrin clathrates of such esters or alcohol derivatives. Preferred esters are straight- or branched-chain alkyl esters containing from 1 to 12, and preferably from 1 to 4, carbon atoms in the esterifying alkyl moiety, e.g. methyl, ethyl, propyl, n-butyl, iso-butyl, n-hexyl, n-heptyl, n-octyl and n-decyl esters, carboalkoxyalkyl esters in which the esterifying moiety is of the general formula —$C_nH_{2n}COOR^1$, wherein n represents an integer of from 1 to 12 and $R^1$ represents a straight- or branched-chain alkyl group containing from 1 to 4 carbon atoms, e.g., carboethoxymethyl, 8-carboethoxyoctyl, 9-carboethoxynonyl and 11-carboethoxyundecyl esters, hydroxy- or alkoxy-alkyl esters in which the esterifying moiety is of the general formula —$C_nH_{2n}OR^2$, wherein $R^2$ represents a hydrogen atom or a straight- or branched-chain alkyl group containing from 1 to 4 carbon atoms and n is as hereinbefore defined, e.g. 2-hydroxyethyl, 4-hydroxybutyl, 5-hydroxypentyl, 6-hydroxyhexyl, 8-hydroxyoctyl and 2-propoxyethyl esters, mono- or dialkylaminoalkyl esters in which the esterifying moiety is of the general formula

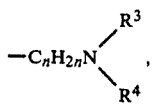

wherein $R^3$ and $R^4$, which may be the same or different, each represents a hydrogen atom or a straight- or branched-chain alkyl group containing from 1 to 4 carbon atoms and n is as hereinbefore defined, e.g. 2-methylaminoethyl and 2-dimethylaminoethyl esters, aralkyl esters containing from 7 to 12 carbon atoms, e.g. benzyl, 1-phenylethyl, 2-phenylethyl, 3-phenylbutyl, 4-phenylbutyl, 1-(2-naphthylethyl) and 2-(1-naphthylethyl) esters, cycloalkyl esters containing from 4 to 7 carbon atoms in the ring, which may be unsubstituted or substituted by at least one alkyl group containing from 1 to 4 carbon atoms, e.g. cyclobutyl, cyclopentyl, cyclohexyl and 3-ethylcyclohexyl esters, and phenyl esters in which the phenyl group is unsubstituted or carries at least one substituent selected from chlorine atoms, trifluoromethyl groups, straight- or branched-chain alkyl groups containing from 1 to 4 carbon atoms and phenyl groups, e.g. phenyl, 2-chlorophenyl, 2,4-dichlorophenyl, 2-tolyl, 4-ethylphenyl and 3-trifluoromethylphenyl esters.

The solvent in the compositions of the invention preferably consists of a single pharmacologically-acceptable alcohol, polar aprotic solvent or middle chain triglyceride, and is preferably anhydrous. Preferred alcohols are those which are liquid at room temperature, with the exclusion of methanol. The most preferred alcohol is ethanol. Preferred polar aprotic solvents are N,N-dimethylacetamide, N,N-dimethylformamide, hexamethylphosphoramide and dimethyl sulphoxide; N,N-dimethylacetamide and dimethyl sulphoxide are particularly preferred.

"Middle chain triglycerides" referred to in this specification and the accompanying claims are preferably triglycerides which are liquid at ambient temperature and in which the esterifying acid or acids, which may be the same or different, may be saturated or unsaturated. Tricaproin and tricaprylin, particularly tricaprylin, are especially preferred.

The concentration of PGI$_2$ analogues in solutions according to the invention is preferably from 0.01 mg/ml to 100 mg/ml; concentrations of from 0.5 mg/ml to 10 mg/ml are particularly preferred.

Cyclodextrin clathrates of the PGI$_2$ analogues may be prepared by dissolving the cyclodextrin in water or an organic solvent which is miscible with water in the presence of triethylamine and adding to the solution the PGI$_2$ analogue in a water-miscible organic solvent, preferably ethanol. The mixture is stirred vigorously and then the desired cyclodextrin clathrate product is isolated by concentrating the mixture under reduced pressure, or by cooling and separating the product by filtration or decantation. The ratio of organic solvent to water may be varied according to the solubilities of the starting materials and products. The temperature of the reaction mixture should not be allowed to exceed 40° C., and is preferably kept at room temperature, during the preparation of the cyclodextrin clathrates. $\alpha$-, $\beta$- or $\gamma$-Cyclodextrins or mixtures thereof may be used in the preparation of the cyclodextrin clathrates.

In the production of cyclodextrin clathrates of PGI$_2$ analogues, the molar ratio of cyclodextrin to PGI$_2$ analogue is generally from 1 to 25:1 and preferably from 3 to 15:1.

The solutions and cyclodextrin clathrates according to the invention may, where appropriate, be used as such in various liquid or solid pharmaceutical formulations or may be used to prepare pharmaceutical formulations by any method known per se. In clinical practice the compositions will normally be administered parenterally, vaginally or rectally.

Pharmaceutical compositions which comprise, as active ingredient, a cyclodextrin clathrate of a PGI$_2$ analogue in association with a pharmaceutically acceptable carrier, constitute a further feature of the present invention.

The following Examples illustrate the present invention. In the Examples "TLC" represents "thin layer chromatography".

EXAMPLE 1

2 mg of PGI$_2$ methyl ester was dissolved in 2 ml of ethanol.

The stabilizing effect on PGI$_2$ methyl ester of dissolution in ethanol was confirmed by a stability test carried out at 60° C. The results were evaluated with respect to the percentage of residual PGI$_2$ methyl ester after heating the ethanol solution and PGI$_2$ methyl ester itself for definite periods of time, the residual percentage being estimated by comparison of the size and intensity of colour of the spots of PGI$_2$ methyl ester and of its degradation products in TLC.

The TLC was carried out with a 0.25 mm plate of Kieselgel F$_{254}$ (Merck) pretreated with a 5% v/v solution of triethylamine in diethyl ether, using as developing solvent a mixture of diethyl ether and acetone (3:1) containing 0.1% v/v triethylamine, and a cupric acetate solution [prepared by dissolving 3 g of copper(II) acetate in 100 ml of a 20% v/v aqueous solution of phosphoric acid] as colour developer. After heating at 60° C., 0.1 ml of the ethanol solution of $PGI_2$ methyl ester was concentrated under reduced pressure and the residue obtained and about 100 μg of the $PGI_2$ methyl ester, which had also been heated at 60° C., were tested by TLC as described above.

The results of the test are given in Table I which follows.

EXAMPLE 2

3.3 mg of $PGI_2$ methyl ester was dissolved in 0.33 ml of N,N-dimethylacetamide.

The stabilizing effect on the $PGI_2$ methyl ester of dissolution in N,N-dimethylacetamide was confirmed in a similar manner to that described in Example 1, but the samples for TLC were prepared as follows: 0.01 ml of the N,N-dimethylacetamide solution of $PGI_2$ methyl ester, previously heated at 60° C. was added to 4 ml of distilled water containing 1% v/v triethylamine and the mixture was extracted with 4 ml of diethyl ether containing 0.1% v/v triethylamine. An appropriate quantity of methanol was added to the aqueous layer thus obtained and the mixture was concentrated under reduced pressure. The residue obtained was tested by TLC.

The results of the test are given in Table I which follows.

EXAMPLE 3

3.29 mg of $PGI_2$ methyl ester was dissolved in 3.29 ml of tricaprylin.

The stabilizing effect on the $PGI_2$ methyl ester of dissolution in tricaprylin was confirmed in a similar manner to that described in Example I, but the samples for TLC were prepared as follows: 0.1 ml of the tricaprylin solution of $PGI_2$ methyl ester, previously heated at 60° C., was added to 5 ml of 80% v/v aqueous ethanol containing 1% v/v triethylamine and the mixture was extracted with n-pentane containing 0.1% v/v triethylamine. The aqueous layer thus obtained was concentrated under reduced pressure and the residue obtained was tested by TLC.

The results of the test are given in Table I which follows.

EXAMPLE 4

A solution of 5.59 mg of $PGI_2$ methyl ester in 1.5 ml of ethanol was added to a solution of 71.69 mg of β-cyclodextrin in 3 ml of distilled water containing 1% v/v triethylamine at room temperature. The reaction mixture was stirred for about 1 minute and then concentrated under reduced pressure at below 35° C. to give 72.85 mg of β-cyclodextrin clathrate of $PGI_2$ methyl ester. The content of $PGI_2$ methyl ester in the product was 7.7% by weight.

By proceeding as described above, 175.58 mg of α-cyclodextrin clathrate of $PGI_2$ methyl ester was prepared from 5.58 mg of $PGI_2$ methyl ester and 184.00 mg of α-cyclodextrin. The content of $PGI_2$ methyl ester in the product was 3.2% by weight.

The stabilizing effect of cyclodextrin clathrate formation on the $PGI_2$ methyl ester was confirmed in a similar manner to that described in Example 1, but the samples for TLC were prepared as follows: After heating at 60° C., about 1.3 mg of the β-cyclodextrin clathrate or about 3.1 mg of the α-cyclodextrin clathrate of $PGI_2$ methyl ester was dissolved in distilled water containing 1% v/v triethylamine and the mixture was extracted with diethyl ether containing 0.1% v/v triethylamine. The extract was concentrated under reduced pressure and the residue obtained was tested by TLC.

The results of the test are given in Table I which follows.

EXAMPLE 5

1.29 mg of $PGI_2$ methyl ester, 1.11 mg of 17(S),20-dimethyl-$PGI_2$ methyl ester, 1.00 mg of 15-(3-propyl)-cyclopentyl-16,17,18,19,20-pentanor-$PGI_2$ methyl ester, 1.13 mg of 16ξ-cyclopentyl-18,19,20-trinor-$PGI_2$ methyl ester and 1.12 mg of 16ξ-methyl-20-chloro-$PGI_2$ methyl ester were dissolved in 2.58 ml, 2.22 ml, 2.00 ml, 2.26 ml and 2.24 ml of ethanol, respectively.

The stabilizing effect on the $PGI_2$ analogues of dissolution in ethanol was confirmed in a similar manner to that described in Example 1 but the stability test was carried out at 40° C.

The results of the test are given in Table II which follows.

EXAMPLE 6

1.69 mg of $PGI_2$ methyl ester, 1.42 mg of 17(S),20-dimethyl-$PGI_2$ methyl ester, 1.19 mg of 15-(3-propyl)-cyclopentyl-16,17,18,19,20-pentanor-$PGI_2$ methyl ester, 1.28 mg of 16ξ-cyclopentyl-18,19,20-trinor-$PGI_2$ methyl ester, 1.30 mg of 16ξ-methyl-20-chloro-$PGI_2$ methyl ester and 1.67 mg of $PGI_2$ N,N-dimethylaminoethyl ester were dissolved in 0.17 ml, 0.14 ml, 0.12 ml, 0.13 ml, 0.13 ml and 0.17 ml of N,N-dimethylacetamide, respectively.

The stabilizing effect on the $PGI_2$ analogues of dissolution in N,N-dimethylacetamide was confirmed in a similar manner to that described in Example 2 but the stability test was carried out at 40° C.

The results of the test are given in Table II which follows.

EXAMPLE 7

3.28 mg of $PGI_2$ methyl ester were dissolved in 0.33 ml of dimethyl sulphoxide.

The stabilizing effect on the $PGI_2$ methyl ester of dissolution in dimethyl sulphoxide was confirmed in the same manner as described in Example 6.

The results of the test are given in Table II which follows.

EXAMPLE 8

71 mg of α-cyclodextrin clathrate containing 3.1% w/w of $PGI_2$ methyl ester, 63 mg of α-cyclodextrin clathrate containing 3.1% w/w of 17(S),20-dimethyl-$PGI_2$ methyl ester, 58 mg of α-cyclodextrin clathrate containing 3.2% w/w of 15-(3-propyl)cyclopentyl-16,17,18,19,20-pentanor-$PGI_2$ methyl ester, 67 mg of α-cyclodextrin clathrate containing 3.1% w/w of 16ξ-cyclopentyl-18,19,20-trinor-$PGI_2$ methyl ester, 67 mg of α-cyclodextrin clathrate containing 3.1% w/w of 16ξ-methyl-20-chloro-$PGI_2$ methyl ester and 69 mg of α-cyclodextrin clathrate of $PGI_2$ N,N-dimethylaminoethyl ester were prepared in the same manner as described in Example 4.

The stabilizing effect of α-cyclodextrin clathrate formation on the $PGI_2$ analogues was confirmed in a similar manner to that described in Example 4 but the stability test was carried out at 40° C.

The results of the test are given in Table II which follows.

EXAMPLE 9

PGI$_2$ methyl ester (5 mg) was dissolved in ethanol (5 ml). The solution was then sterilized by passage through a bacteria-retaining filter and placed in 0.1 ml portions in 1 ml ampoules, to give 100 μg of PGI$_2$ methyl ester per ampoule. The ampoules were sealed. The contents of an ampoule diluted to a suitable volume, with e.g. 1 ml of tris-HCl-buffer solution (pH 8.6), gave a solution ready for administration by injection.

EXAMPLE 10

Other compositions according to the invention were obtained by proceeding as described in Example 9, but replacing the PGI$_2$ methyl ester by 17(S),20-dimethyl-PGI$_2$ methyl ester, 15-(3-propyl)cyclopentyl-16,17,18,19,20-pentanor-PGI$_2$ methyl ester, 16ξ-cyclopentyl-18,19,20-trinor-PGI$_2$ methyl ester and 16ξ-methyl-20-chloro-PGI$_2$ methyl ester.

EXAMPLE 11

Other compositions according to the invention were obtained by proceeding as described in Example 9 or 10, but replacing the ethanol by N,N-dimethylacetamide, dimethyl sulphoxide and tricaprylin.

EXAMPLE 12

333 mg of α-cyclodextrin clathrate of PGI$_2$ methyl ester (containing 10 mg of PGI$_2$ methyl ester) were dissolved in distilled water containing 1% v/v triethylamine and the solution obtained, after being made up to 50 ml, was then sterilized by passage through a bacteria-retaining filter and placed in 0.5 ml portions in 5 ml ampoules. The solution was immediately lyophilized to give 100 μg of PGI$_2$ methyl ester per ampoule. The ampoules were sealed. The contents of an ampoule dissolved in a suitable volume, e.g. 1 ml of tris-HCl-buffer solution (pH 8.6), gave a solution ready for administration by injection.

EXAMPLE 13

Other compositions according to the invention were obtained by proceeding as described in Example 12, but replacing the PGI$_2$ methyl ester by 17(S),20-dimethyl-PGI$_2$ methyl ester, 15-(3-propyl)cyclopentyl-16,17,18,19,20-pentanor-PGI$_2$ methyl ester, 16ξ-cyclopentyl-18,19,20-trinor-PGI$_2$ methyl ester, 16ξ-methyl-20-chloro-PGI$_2$ methyl ester and PGI$_2$ N,N-dimethylaminoethyl ester.

TABLE I

| | Percentage of PGI$_2$ methyl ester remaining after heating (60° C.) | | | | | | | |
|---|---|---|---|---|---|---|---|---|
| | (hours) | | (days) | | | | | |
| Sample | 3 | 6 | 1 | 2 | 4 | 7 | 10 | 14 |
| PGI$_2$ methyl ester | <5 | <5 | | | | | | |
| ethanol solution of PGI$_2$ methyl ester | 100 | 100 | 99–98 | 99–98 | 99–98 | 99–98 | 98 | 97–95 |
| N,N—dimethylacetamide solution of PGI$_2$ methyl ester | 99–98 | 99–98 | 99–98 | 95–90 | 90–80 | 67–50 | | 34 |
| tricaprylin solution of PGI$_2$ methyl ester | 90–80 | 90–80 | 67–50 | 34 | 25 | <5 | | |
| α-cyclodextrin clathrate of PGI$_2$ methyl ester | 100 | 100 | 100 | 97–95 | 97–95 | 97–95 | 97–95 | 95–90 |
| β-cyclodextrin clathrate of PGI$_2$ methyl ester | 100 | 95–90 | 90–80 | 80–67 | 80–67 | 80–67 | 67–50 | 50 |

TABLE II

| | Percentage of PGI$_2$ analogues remaining after heating (40° C.) | | | | | | | |
|---|---|---|---|---|---|---|---|---|
| | (hours) | | (days) | | | | | |
| Sample | 3 | 6 | 1 | 2 | 4 | 7 | 10 | 14 |
| A | 67–50 | <25 | <10 | 0 | | | | |
| ethanol solution of A | 100 | >99 | >99 | >99 | 98–97 | 90 | 90 | |
| N,N—dimethylacetamide solution of A | 100 | 100 | 100 | 100 | 100 | 99–98 | 98–97 | 95 |
| dimethyl sulphoxide solution of A | 100 | 100 | 100 | >99 | >99 | 98–97 | 97–95 | |
| α-cyclodextrin clathrate of A | 100 | 100 | 100 | 98–97 | 97–95 | 95 | 97–95 | 95–90 |
| B | 50–34 | <25 | <10 | 0 | | | | |
| ethanol solution of B | 100 | 100 | 100 | 100 | 98–97 | 95–90 | 95–90 | |
| N,N—dimethylacetamide solutioin of B | 100 | 100 | 100 | 100 | 100 | 98–97 | 98–97 | 95–90 |
| α-cyclodextrin clathrate of B | 100 | 100 | 100 | 97–95 | 97–95 | 95–90 | 95–90 | 95–90 |
| C | 80–67 | <25 | <10 | 0 | | | | |
| ethanol solution of C | 100 | 100 | 100 | 100 | 98–97 | 97–95 | 95–90 | |
| N,N—dimethylacetamide solution of C | 100 | 100 | 100 | 100 | 100 | 98–97 | 97–95 | 95–90 |
| α-cyclodextrin clathrate of C | 100 | 100 | 100 | 97–95 | 95–90 | | 95–90 | 95–90 |
| D | 50 | <25 | <10 | 0 | | | | |
| ethanol solution of D | 100 | 100 | 100 | 100 | 98–97 | 95–90 | 90 | |
| N,N—dimethylacetamide solution of D | 100 | 100 | 100 | 100 | 100 | 98–97 | 97–95 | 95–90 |
| α-cyclodextrin clathrate of D | 100 | 100 | 100 | 90 | 90–80 | 95–90 | 90–80 | 80–67 |
| E | 50–34 | <25 | <10 | 0 | | | | |
| ethanol solution of E | 100 | 100 | 100 | 100 | 97–95 | 90–80 | 90–80 | |
| N,N—dimethylacetamide solution of E | 100 | 100 | 100 | 100 | 100 | 97–95 | 95–90 | 80 |
| α-cyclodextrin clathrate of E | 100 | 100 | 100 | 95–90 | 90–80 | 90–80 | 90–80 | 80–67 |
| F | 100 | 100 | 67 | <50 | <10 | 0 | | |
| N,N—dimethylacetamide solution of F | 100 | 100 | 100 | 100 | 100 | 97–95 | 97–95 | 95–90 |

TABLE II-continued

| Sample | Percentage of PGI₂ analogues remaining after heating (40° C.) | | | | | | |
|---|---|---|---|---|---|---|---|
| | (hours) | | (days) | | | | |
| | 3 | 6 | 1 | 2 | 4 | 7 | 10 | 14 |
| α-cyclodextrin clathrate of F | 100 | 100 | 90–80 | 90–80 | 90–80 | 90–80 | 80–67 | 80–67 |

[A] PGI₂ methyl ester
[B] 17(S),20-dimethyl-PGI₂ methyl ester
[C] 15-(3-propyl)cyclopentyl-16,17,18,19,20-pentanor-PGI₂ methylester
[D] 16ξ-cyclopentyl-18,19,20-trinor-PGI₂ methyl ester
[E] 16ξ-methyl-20-chloro-PGI₂ methyl ester
[F] PgI₂ N,N—dimethylaminoethyl ester.

We claim:

1. A stabilized composition which contains a PGI₂ analogue in solution in a solvent consisting essentially of at least one pharmacologically-acceptable alcohol, N,N-dimethylacetamide, N,N-dimethylformamide, hexamethylphosphoramide, dimethyl sulphoxide, or a middle chain triglyceride, or which is a cyclodextrin clathrate of a PGI₂ analogue, said PGI₂ analogue being selected from the group consisting of PGI₂ compounds in which the carboxyl group of PGI₂, 5(E)PGI₂, 11-deoxy-PGI₂, 13,14-dihydro-PGI₂, trans-delta2-PGI₂, 16-chloro-PGI₂, 7-methyl-PGI₂ and 7a-homo-PGI₂ is esterified or replaced by CH₂OH, compounds differing from PGI₂ 5(E)-PGI₂, 11-deoxy-PGI₂, 13,14-dihydro-PGI₂, and trans-delta2-PGI₂ by having a longer or shorter side chain attached to the 6- or 12-position, and in which the side chain attached to the 6-position may carry an alkyl substituent and the side chain attached to the 12-position may carry an alkyl, hydroxy, cycloalkyl, phenyl or phenoxy substituent, and such compounds in which the carboxyl group is esterified or replaced by CH₂OH.

2. A pharmaceutical composition useful for the treatment of arteriosclerosis, cardiac failure or thrombosis which comprises, as active ingredient, an effective amount of a cyclodextrin clathrate of a PGI₂ analogue as specified in claim 1 in association with a pharmaceutically acceptable carrier.

3. A cyclodextrin clathrate of a PGI₂ analogue, said PGI₂ analogue being selected from the group consisting of compounds in which the carboxy group of PGI₂ is esterified or replaced by an alcohol group (—CH₂OH), compounds which possess carbon skeletons similar to that of PGI₂ with a corresponding carboxy group but in which the side chains attached to the 6- and 12-positions may be longer or shorter than those of PGI₂, and in which the side chain attached to the 6-position may carry an alkyl substituent and the side chain attached to the 12-position may carry an alkyl, hydroxy, cycloalkyl, phenyl or phenoxy substituent, and such compounds in which the carboxy group is esterified or replaced by an alcohol group, and corresponding 5(E)-PGI₂ compounds, corresponding 11-deoxy-PGI₂ compounds, corresponding 13,14-dihydro-PGI₂ compounds, corresponding trans-Δ²-PGI₂ compounds, corresponding 16-chloro-PGI₂ compounds, corresponding 7-methyl-PGI₂ compounds, and corresponding 7a-homo-PGI₂ compounds.

4. A pharmaceutical composition useful for the treatment of arteriosclerosis, cardiac failure or thrombosis which comprises, as active ingredient, an effective amount of a cyclodextrin clathrate of a PGI₂ analogue in association with a pharmaceutically acceptable carrier, said PGI₂ analogue being selected from the group consisting of compounds in which the carboxy group of PGI₂ is esterified or replaced by an alcohol group (—CH₂OH), compounds which possess carbon skeletons similar to that of PGI₂ with a corresponding carboxy group but in which the side chains attached to the 6- and 12-positions may be longer or shorter than those of PGI₂, and in which the side chain attached to the 6-position may carry an alkyl substituent and the side chain attached to the 12-position may carry an alkyl, hydroxy, cycloalkyl, phenyl or phenoxy substituent, and such compounds in which the carboxy group is esterified or replaced by an alcohol group, and corresponding 5(E)-PGI₂ compounds, corresponding 11-deoxy-PGI₂ compounds, corresponding 13,14-dihydro-PGI₂ compounds, corresponding trans-Δ²-PGI₂ compounds, corresponding 16-chloro-PGI₂ compounds, corresponding 7-methyl-PGI₂ compounds, and corresponding 7a-homo-PGI₂ compounds.

5. A cyclodextrin clathrate of a PGI₂ analogue in the form of an ester or alcohol derivative of PGI₂, 2a-homo-PGI₂, 7a-homo-PGI₂, 2-nor-PGI₂, 2-methyl-PGI₂, 3-methyl-PGI₂, 5-methyl-PGI₂, 7-methyl-PGI₂, 15 methyl-PGI₂, 16-methyl-PGI₂, 17-methyl-PGI₂, 16,16-dimethyl-PGI₂, 17,20-dimethyl-PGI₂, 17-ethyl-PGI₂, 20 hydroxy-PGI₂, 16-chloro-PGI₂, 15-cyclopentyl-16,17,18,19,20-pentanor-PGI₂, 15-cyclohexyl-16,17,18,19,20-pentanor-PGI₂, 15-(1 butyl)cyclobutyl-16,17,18,19,20-pentanor-PGI₂, 15-(2-ethyl)cyclopentyl-16,17,18,19,20-pentanor-PGI₂, 15-(3-ethyl)cyclopentyl-16,17,18,19,20-pentanor-PGI₂, 15-(3-propyl)cyclopentyl-16,17,18,19,20-pentanor-PGI₂, 15-(3-ethyl)cyclohexyl-16,17,18,19,20-pentanor-PGI₂, 15-(4-ethyl)cyclohexyl-16,17,18,19,20-pentanor-PGI₂, 16-cyclohexyl-17,18,19,20-tetranor-PGI₂, 16-cyclopentyl-18,19,20-trinor-PGI₂, 17-cyclohexyl-18,19,20-trinor-PGI₂, 17-cyclohexyl-19,20-dinor-PGI₂, 16-methyl-17-cyclohexyl-18,19,20-trinor-PGI₂, 19-cyclohexyl-20-nor-PGI₂, 16-phenyl-17,18,19,20-tetranor-PGI₂, 16-phenoxy-17,18,19,20-tetranor-PGI₂, 16-(4-chlorophenoxy)-17,18,19,20-tetranor-PGI₂, 16-(3-trifluoromethylphenoxy)-17,18,19,20-tetranor-PGI₂ or of a corresponding (5E)-PGI₂ analogue, corresponding 11-deoxy-PGI₂ analogue, corresponding 13,14-dihydro-PGI₂ analogue or corresponding trans-Δ²-PGI₂ analogue.

6. A cyclodextrin clathrate according to claim 5 wherein the ester is a straight- or branched-chain alkyl ester containing from 1 to 12 carbon atoms in the esterifying alkyl moiety, a carboalkoxyalkyl ester in which the esterifying moiety is of the general formula —$C_nH_{2n}COOR^1$ (wherein n represents an integer from 1 to 12 and $R^1$ represents a straight- or branched-chain alkyl group containing from 1 to 4 carbon atoms), a hydroxy- or alkoxy-alkyl ester in which the esterifying moiety is of the general formula —$C_nH_{2n}OR^2$ (wherein $R^2$ represents a hydrogen atom or a straight- or branched-chain alkyl group containing from 1 to 4 carbon atoms and n is as hereinbefore defined), a mono- or di-alkylaminoalkyl ester in which the esterifying moiety is of the general formula

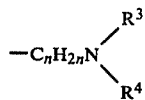

(wherein R³ and R⁴, which may be the same or different, each represents a hydrogen atom or a straight- or branched-chain alkyl group containing from 1 to 4 carbon atoms and n is as hereinbefore defined), an aralkyl ester containing from 7 to 12 carbon atoms, a cycloalkyl ester containing from 4 to 7 carbon atoms in the ring, which may be unsubstituted or substituted by at least one alkyl group containing from 1 to 4 carbon atoms, or a phenyl ester in which the phenyl group is unsubstituted or carries at least one substituent selected from chlorine atoms, trifluoromethyl groups, straight- or branched-chain alkyl groups containing from 1 to 4 carbon atoms and phenyl groups.

7. A cyclodextrin clathrate according to claim 6 wherein the ester is an alkyl ester containing from 1 to 4 carbon atoms in the esterifying alkyl moiety.

8. A cyclodextrin clathrate of a PGI₂ analogue as specified in claim 5 in which the molar ratio of cyclodextrin to PGI₂ analogue is from 1 to 25:1.

9. A cyclodextrin clathrate according to claim 8 in which the molar ratio is from 3 to 15:1.

10. A cyclodextrin clathrate of a PGI₂ analogue specified in claim 6 or 7 in which the molar ratio of cyclodextrin to PGI₂ analogue is from 1 to 25:1.

11. A pharmaceutical composition useful for the treatment of arteriosclerosis, cardiac failure or thrombosis which comprises, as active ingredient, an effective amount of a cyclodextrin clathrate of a PGI₂ analogue as specified in claim 5 in association with a pharmaceutically acceptable carrier.

12. A stabilized composition which contains a PGI₂ analogue in the form of an ester or alcohol derivative of PGI₂, 2a-homo-PGI₂, 7a-homo-PGI₂, 2-nor-PGI₂, 2-methyl-PGI₂, 3-methyl-PGI₂, 5-methyl-PGI₂, 7-methyl-PGI₂, 15-methyl-PGI₂, 16-methyl-PGI₂, 17-methyl-PGI₂, 16,16-dimethyl-PGI₂, 17,20-dimethyl-PGI₂, 17-ethyl-PGI₂, 20-hydroxy-PGI₂, 16-chloro-PGI₂, 20-chloro-PGI₂, 16-methyl-20-chloro-PGI₂, 15-cyclopentyl-16,17,18,19,20-pentanor-PGI₂, 15-cyclohexyl-16,17,18,19,20-pentanor-PGI₂, 15-(1 butyl)cyclobutyl-16,17,18,19,20-pentanor-PGI₂, 15-(2-ethyl)cyclopentyl-16,17,18,19,20-pentanor-PGI₂, 15-(3-ethyl)cyclopentyl-16,17,18,19,20-pentanor-PGI₂, 15-(3-propyl)cyclopentyl-16,17,18,19,20-pentanor-PGI₂, 15-(3-ethyl)cyclohexyl-16,17,18,19,20-pentanor-PGI₂, 15-(4-ethyl)cyclohexyl-16,17,18,19,20-pentanor-PGI₂, 16-cyclohexyl-17,18,19,20-tetranor-PGI₂, 16-cyclopentyl-18,19,20-trinor-PGI₂, 17-cyclohexyl-18,19,20-trinor-PGI₂, 17-cyclohexyl-19,20-dinor-PGI₂, 16-methyl-17-cyclohexyl-18,19,20-trinor-PGI₂, 19-cyclohexyl-20-nor-PGI₂, 16-phenyl-17,18,19,20-tetranor-PGI₂, 16-phenoxy-17,18,19,20-tetranor-PGI₂, 16-(4-chlorophenoxy)-17,18,19,20-tetranor-PGI₂, 16-(3-trifluoromethylphenoxy)-17,18,19,20-tetranor-PGI₂ or of a corresponding (5E)-PGI₂ analogue, corresponding 11-deoxy-PGI₂ analogue, corresponding 13,14-dihydro-PGI₂ analogue or corresponding trans-Δ²-PGI₂ analogue in solution in a pharmacologically-acceptable alcohol, N,N-dimethyl acetamide, N,N-dimethylformamide, hexamethyl phosphoramide, dimethyl sulphoxide, or a middle chain triglyceride.

13. A composition according to claim 12 wherein the solvent is ethanol.

14. A composition according to claim 12 wherein the solvent is dimethyl sulphoxide.

15. A composition according to claim 12 wherein the solvent is N,N-dimethylacetamide.

16. A composition according to claim 12 wherein the solvent consists of at least one middle chain triglyceride which is liquid at ambient temperature and in which the esterifying acid or acids, which may be the same or different, may be saturated or unsaturated.

17. A composition according to claim 12 wherein the solvent is tricaproin.

18. A composition according to claim 12 wherein the solvent is tricaprylin.

19. A composition according to claim 12 wherein the concentration of PGI₂ analogue in solution is from 0.01 mg/ml to 100 mg/ml.

20. A composition according to claim 19 wherein the concentration in solution is from 0.5 mg/ml to 10 mg/ml.

* * * * *